United States Patent [19]

Kaneko et al.

[11] 4,332,951

[45] Jun. 1, 1982

[54] ANTITUMOR AGENTS

[75] Inventors: Takushi Kaneko, Fayetteville; John M. Essery, Pleasantville; Henry Schmitz, Syracuse; Terrence W. Doyle, Fayetteville, all of N.Y.

[73] Assignee: Bristol-Myers Company, New York, N.Y.

[21] Appl. No.: 223,594

[22] Filed: Jan. 9, 1981

Related U.S. Application Data

[62] Division of Ser. No. 95,917, Nov. 19, 1979, Pat. No. 4,267,113.

[51] Int. Cl.[3] .................. C07D 498/22; C07D 493/10; C07D 493/20

[52] U.S. Cl. .................................................... 548/218

[58] Field of Search ......................................... 548/218

[56] References Cited

U.S. PATENT DOCUMENTS 3,428,652 2/1969 Sigg et al. ........................ 260/345.2

4,129,577 12/1978 Ellison et al. .................... 260/345.2

FOREIGN PATENT DOCUMENTS 1063255 3/1967 United Kingdom ............. 260/345.2

OTHER PUBLICATIONS

Flury, et al., J. Chem. Soc., Chem. Comm., pp. 26–27, (1965).

Dawkins, et al., J. Chem. Soc. (c), pp. 369–375, (1970).

Sigg et al., Helvetica Chimica Acta, 48, pp. 962–988. (1965).

*Primary Examiner*—Donald G. Daus
*Assistant Examiner*—Sharon A. Gibson
*Attorney, Agent, or Firm*—David M. Morse

[57] ABSTRACT

Novel 3-hydroxyiminoscirpen-4$\beta$, 15-diol esters and derivatives thereof are provided for use as antitumor agents. Also provided are processes for producing the above compounds and methods for using them to inhibit malignant tumors in mammals.

1 Claim, No Drawings

ANTITUMOR AGENTS

CROSS-REFERENCE TO RELATED APPLICATION

This application is a division of our copending application Ser. No. 95,917, filed Nov. 19, 1979, now U.S. Pat. No. 4,267,113.

BACKGROUND OF THE INVENTION

1. Field of the Invention

The present invention relates to novel trichothecene derivatives, to processes for their production and to their use as antitumor agents for the inhibition of malignant tumors in mammals.

2. Description of the Prior Art

The trichothecene derivatives of the present invention all contain a 9,10 double bond and a 12,13-epoxy function. The basic skeleton and numbering system for this class of trichothecenes is shown below.

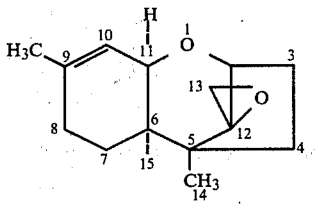

Various examples of both naturally occurring and semisynthetic compounds of this class have been described in the literature. Illustrative of the more relevant publications are the following:

1. The compound anguidine (also called diacetoxyscirpenol) having the formula

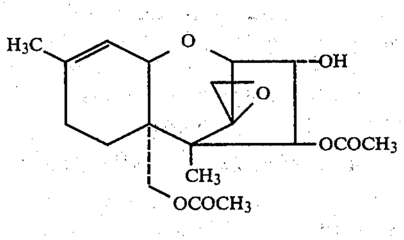

is disclosed as an antitumor agent in U.K. Pat. No. 1,063,255. Phase I clinical trials of anguidine in the United States have been reported in *Proc. Amer. Assoc. Cancer Res.* 17:90 (1976) and *Proc. Amer. Assoc. Cancer Res.* 18:296 (1977). Also disclosed (at least generically) are various derivatives of anguidine such as anguidol (also called scirpentriol or 3α,4β,15-trihydroxy-12,13-epoxytrichothec-9-ene), monodesacetylanguidine (presumably 15-acetoxy-3α,4β-dihydroxy-12,13-epoxytrichothec-9-ene or monoacetoxyscirpendiol) and esters of anguidine, anguidol and monodesacetylanguidine.

Monoacetoxyscirpenol and various esters of scirpentriol are also disclosed in *J. Agric. Food Chem.* 24(1): 97–103 (1976) as mycotoxins.

2. Japanese Published Applications Nos. J4 9,134,891 and J4 9,134,892 disclose T2 and HT2 toxins of the formula

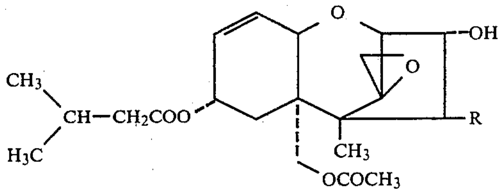

wherein R is —OH or

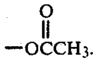

The compounds are said to be useful as antiviral agents.

3. U.S. Pat. No. 4,129,577 discloses anguidine derivatives of the formula

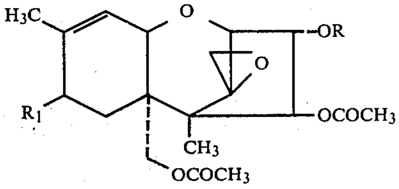

wherein $R_1$ is H or

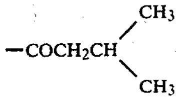

and R is an alkyl or aromatic group or is an acyl group

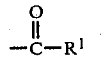

in which $R^1$ is an aliphatic, cycloaliphatic or aromatic group or a carbamate group —CONH-$R^1$. The compounds are useful as cytotoxic agents.

4. U.S. Pat. No. 3,428,652 discloses anguidine derivatives of the formula

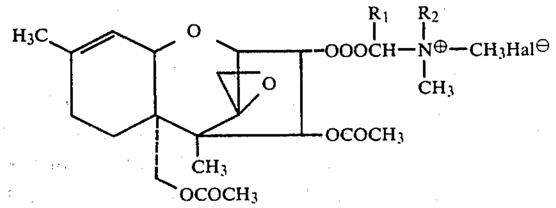

wherein $R_1$ is H and $R_2$ is methyl or, $R_1$ and $R_2$ together represent propylene, and Hal is Cl, Br or I. The compounds are reported to have antitumor activity.

5. Toxins isolated from culture filtrates of *F. scirpi* and having the formula

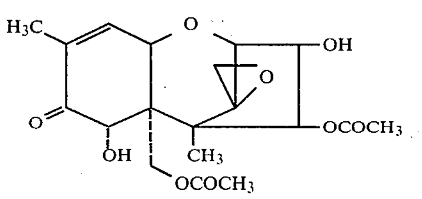

and

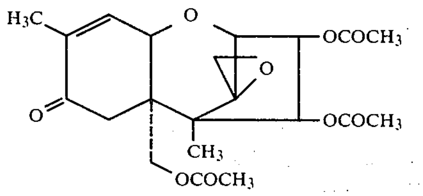

are disclosed in *J. Chem. Soc* (C), 375 (1970).

6. Trichothecene derivatives of the formula

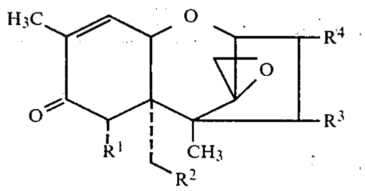

wherein $R^1$, $R^2$, $R^3$ and $R^4$ are -OH or -$OCOCH_3$ are disclosed in *Biochemical Pharmacology* 24:959–962 (1972) as having larvicidal activity. The degree of activity is said to be greatest in the compound where $R^1{=}R^2{=}R^3{=}R^4{=}OH$ and least in the fully acetylated compound. It is suggested in the publication that the order of cytotoxic activity in this series is the same as the order of larvicidal activity.

7. The 12,13-epoxytrichothecenes of the general formula

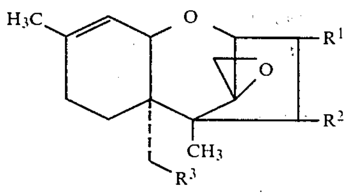

wherein $R^1$ and $R^3$ are H, OH or esterified OH and $R^2$ is OH, =O or esterified OH are described in *Biochemical and Biophysical Research Communications* 57(3):838–844 (1974)as inhibitors of protein synthesis. The publication indicates that substitution of a carbonyl group at the C-8 position of the above compounds results in a moderate loss of activity and that substitution of a carbonyl group at C-4 results in complete loss of activity.

8. *Helvetica Chimica Acta* 48:962–988 (1965) discloses the 4-keto compound of the formula

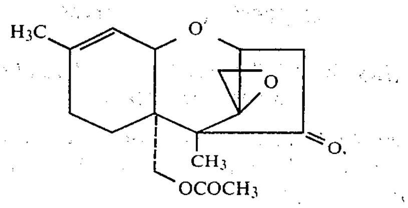

the 3-keto compounds of the formulae

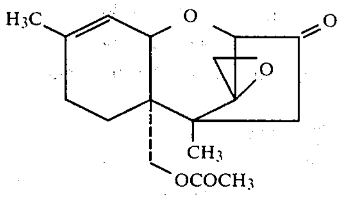

and

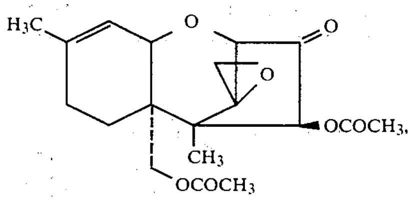

and the oxime compound of the formula

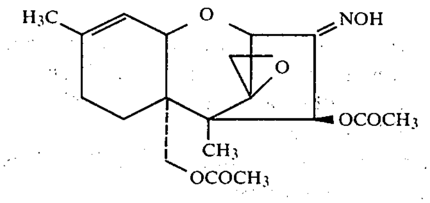

The above-mentioned 3-keto diester is also disclosed in *J. Chem. Soc. Chem. Comm.*, 1965, pg. 26–27 and in *J. Chem. Soc.* (C), pg. 369–375 (1970). None of the publications provide any information as to biological properties of the keto or oxime compounds.

SUMMARY OF THE INVENTION

The present invention provides novel trichothecene derivatives of the general formula

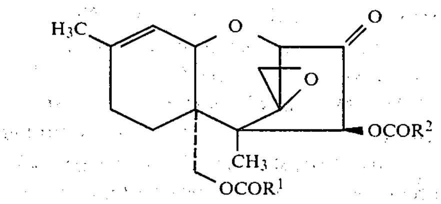

I wherein $R^1$ and $R^2$ are each independently (lower)alkyl; halo(lower)alkyl; alkenyl of the formula $-CR^3{=}CR^4R^5$ in which $R^3$ is hydrogen, (lower)alkyl or 1'-halo(lower)alkyl and $R^4$ and $R^5$ are each independently hydrogen or (lower)alkyl; alkynyl of the formula $-C{\equiv}CR^6$ in which $R^6$ is hydrogen or (lower)alkyl; or a radical of the formula $Ar-(CH_2)_m-$ in which m is 0 or an integer from one to four and Ar is

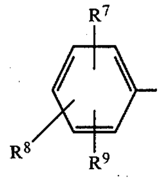
or
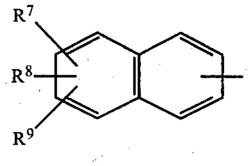

wherein $R^7$, $R^8$ and $R^9$ are each independently hydrogen, halogen, (lower)alkyl or (lower)alkoxy, with the proviso that $R^1$ and $R^2$ may not both be methyl.

In another aspect the present invention provides oxime compounds of the general formulae

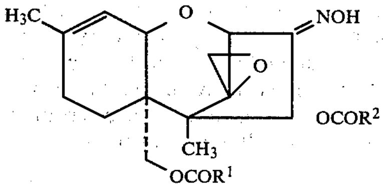
II and

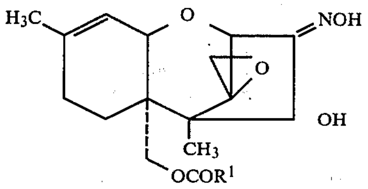
III wherein $R^1$ and $R^2$ are each independently (lower)alkyl; halo(lower)alkyl; alkenyl of the formula $-CR^3{=}CR^4R^5$ in which $R^3$ is hydrogen, (lower)alkyl or 1'-halo(lower)alkyl and $R^4$ and $R^5$ are each independently hydrogen or (lower)alkyl; alkynyl of the formula $-C{\equiv}CR^6$ in which $R^6$ is hydrogen or (lower)alkyl; or a radical of the formula $Ar-(CH_2)_m-$ in which m is 0 or an integer from one to four and Ar is

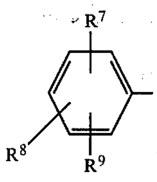
or
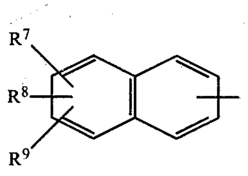

wherein $R^7$, $R^8$ and $R^9$ are each independently hydrogen, halogen, (lower)alkyl or (lower)alkoxy, with the proviso that $R^1$ and $R^2$ may not both be methyl.

In still another aspect of the present invention provides compounds of the formula

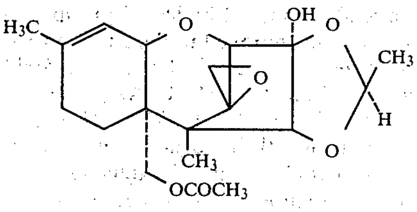
IV

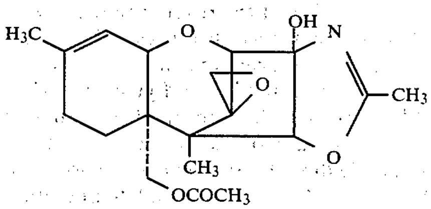
V

The compounds of formulae I–V are antitumor agents for treatment of malignant tumors in mammals.

DETAILED DESCRIPTION

The various substituent groups disclosed above in connection with the novel compounds of the present invention may be further defined as follows:

(a) Halo or halogen includes chlorine, bromine, fluorine and iodine;

(b) (Lower)alkyl includes both straight and branched chain saturated aliphatic hydrocarbon radicals having from 1 to 4 carbon atoms inclusive, e.g. methyl, ethyl, n-propyl, isopropyl or n-butyl;

(c) (Lower)alkoxy includes $C_1$–$C_4$ alkoxy radicals, the alkyl portion of such radicals being defined as in (b) above. Examples include methoxy, ethoxy, n-propoxy, isopropoxy and n-butoxy;

(d) Halo(lower)alkyl includes (lower)alkyl radicals as defined under (b) where one or more hydrogen atoms are substituted by halogen as defined under (a). Examples include $-CF_3$, $-CCl_3$, $-CH_2Cl$, $-CHCl_2$, $-CH_2CH_2Cl$, $-CH_2CF_3$, $-CH_2CH_2CHClCH_3$ or $-CH_2CHClCH_2CH_3$; and (e) The phenyl and naphthyl groups above may be optionally substituted by one, two or three non-hydrogen substituents at any of the available positions of the ring system. The naphthyl radical may be either the $\alpha$- or $\beta$-isomer. Preferred aryl radicals are those which are unsubstituted or which have one non-hydrogen substituent.

Certain compounds within the scope of formulae I–III may contain asymmetric carbon atoms (e.g. when $R^1$ or $R^2$ contains four or more carbon atoms) and, in such cases, the compounds may exist in the form of the individual optical isomers as well as the racemates.

The compounds of formula I may be prepared by reacting the appropriate 3$\alpha$-hydroxy ester starting material of the formula

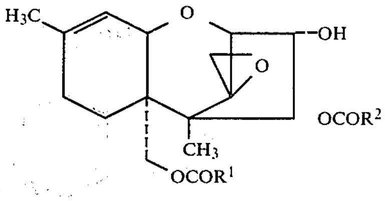
VI with about one equivalent of a mild oxidizing agent in an inert organic solvent.

In general any mild oxidizing agent capable of converting a sterically hindered hydroxyl group to a carbonyl group may be employed in the above process. A particularly preferred reagent is dimethyl sulfoxide-trifluoroacetic anhydride (DMSO-TFAA) which is described in *J. Org. Chem.* 41(20): 3329 (1976). This reagent may be conveniently used in a dry inert organic solvent such as methylene chloride, toluene or tetrahydrofuran at temperatures of from about −78° C. to −50° C. Upon addition of the reagent to the ester VI, a dimethylalkoxysulfonium salt is formed which on treatment with base (e.g. an organic amine such as triethylamine) is rapidly converted in good yields to the corresponding 3-keto product I. Other mild oxidizing agents such as dimethyl sulfoxideacetic anhydride or N-chlorosuccinimide dimethylsulfide may be used in place of the DMSO-TFAA. The preferred temperature for oxidation with dimethylsulfoxide-acetic anhydride is about 0° C. while room temperature is preferred when N-chlorosuccinimide dimethylsulfide is used. Other reaction temperatures than those mentioned above may be successfully employed in the oxidation reaction, but product yields may be reduced from those achieved under the preferred conditions.

Oxime derivatives of formulae II and III may be prepared by reacting the appropriate ester I with hydroxylamine in a suitable inert solvent such as aqueous methanol. A mixture of syn- and anti- oximes of formula II is obtained which, in a suitable solvent (e.g. aqueous methanol), are partially hydrolyzed to give a mixture of syn- and anti-4β-hydroxyoximes III.

Compound IV is prepared by reacting the 3-keto compound of the formula

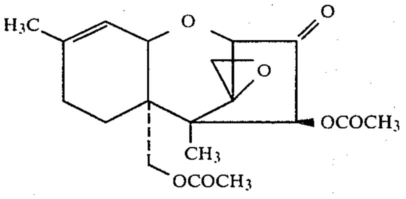

VII with sodium cyanoborohydride in an acidic isopropyl alcoholtetrahydrofuran solvent system.

Compound V is prepared by reacting the 3-keto compound VII with sodium cyanoborohydride and ammonium acetate in methanol.

Starting material 3α-hydroxy esters of general formula VI are known in the art or are prepared by methods well-known to those skilled in the art. Examples of suitable methods are provided below under "Preparation of Starting Materials", but in general the esters may be prepared as shown in the following schemes:

Scheme I

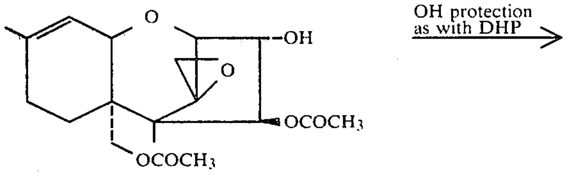

anguidine

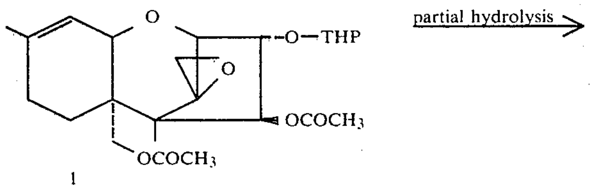

1

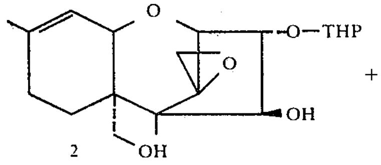

2

+

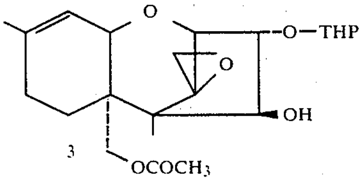

3

Scheme II ($R^1 = R^2$)

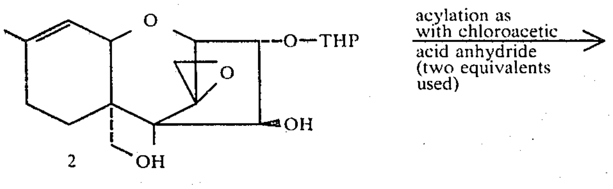

2

-continued

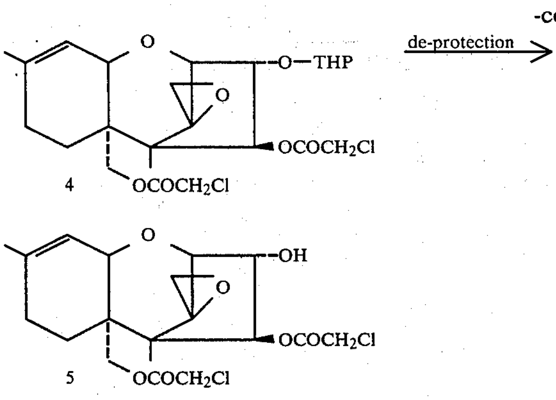

4

5

Scheme III ($R^1 \neq R^2$)

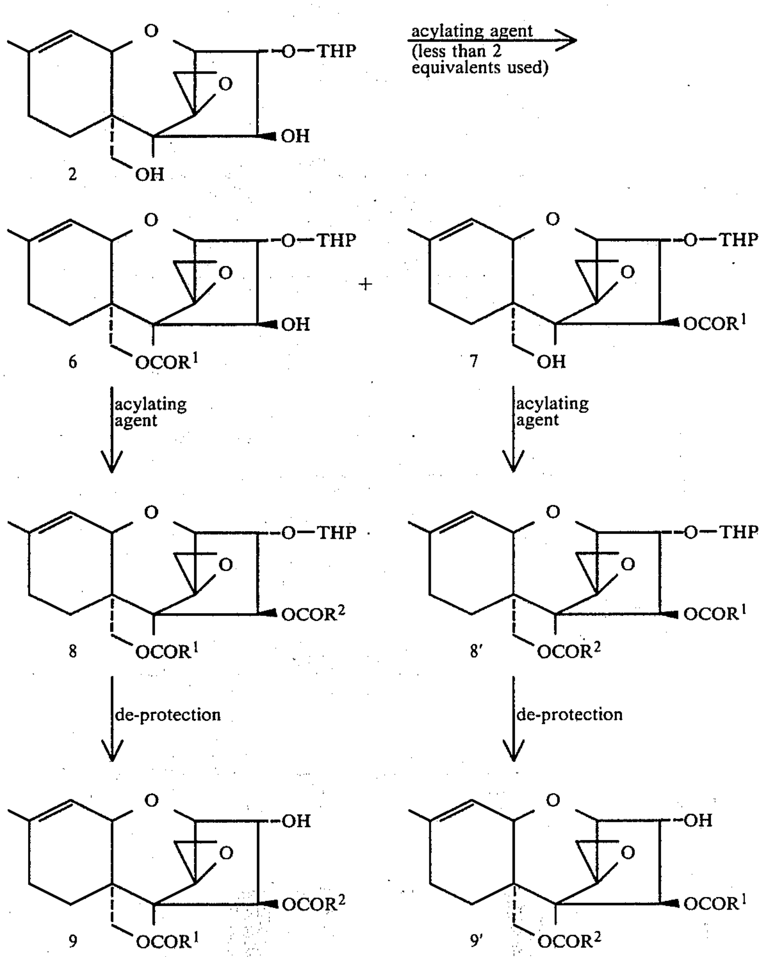

2 6 + 7 8 8' 9 9'

EXPLANATION OF SCHEMES I-III

Using anguidine as the starting material, other 4β,15-diacylated esters of formula VI may be prepared by protecting the 3-OH group as by conversion to a tetrahydropyranyl ether (1), and then subjecting the 3α-THP derivative to partial basic hydrolysis to give a mixture of the 4β-OH (3) and 4β,15-OH (2) derivatives.

Compound 2 may then be acylated in accordance with conventional methods with about two equivalents of a suitable acylating derivative of a carboxylic acid R-COOH to produce a 4β,15-diacylated derivative 4 which may then be de-protected to give 5. The acylation is typically carried out with an acid halide or acid anhydride, preferably in the presence of an organic base such as pyridine or lutidine. Scheme II results in formation of a 4,15-diacylated ester of general formula VI having $R^1=R^2$.

To prepare esters of formula VI where $R^1 \neq R^2$, the 4β,15-diol 2 may be acylated with less than two equivalents of acylating agent to give a mixture of monoacylated derivatives 6 and 7 as shown in Scheme III. These derivatives can be separated chromatographically and then treated with a second acylating agent to give the diacylated derivatives 8 and 8'. Upon de-protection the products 9 and 9' containing mixed acyl groups are produced.

Mixed diacylated esters of formula VI where $R^1$ is methyl may also be prepared by acylation and de-protection of compound 3.

BIOLOGICAL ACTIVITY

Representative compounds of the present invention were tested for antitumor activity against the transplantable mouse tumors P-388 leukemia, L-1210 leukemia and Lewis lung carcinoma and the results of these tests are shown below in Tables I-XI. The methodology used generally followed the protocols of the National Cancer Institute (see, for example, *Cancer Chemotherapy Rep. Part* 3, 3:1-103 (1972)). The essential experimental details are given at the bottom of the tables.

TABLE I

Effect of Compounds of Example 6 on P-388 Leukemia

| Material | Dose mg/kg/inj | MST Days | Effect MST % T/C | Average Weight Change,g | Survivors Day 5 |
|---|---|---|---|---|---|
| Compound of Example 6 (first component) | 6.4 | 13.5 | 150 | +0.8 | 6/6 |
| | 3.2 | 12.0 | 133 | +0.4 | 6/6 |
| | 1.6 | 10.0 | 111 | +1.0 | 5/6 |
| | 0.8 | 10.0 | 111 | +1.8 | 6/6 |
| | 0.4 | 9.0 | 100 | +2.8 | 6/6 |
| | 0.2 | 9.0 | 100 | +2.3 | 6/6 |
| | 0.1 | 9.0 | 100 | +3.1 | 6/6 |
| | 0.05 | 9.0 | 100 | +2.2 | 6/6 |
| Compound of Example 6 (second component) | 3.2 | 12.0 | 133 | +2.3 | 5/5 |
| | 1.6 | 9.0 | 100 | +2.2 | 6/6 |
| | 0.8 | 9.0 | 100 | +2.2 | 6/6 |
| | 0.4 | 9.0 | 100 | +1.8 | 6/6 |
| | 0.2 | 9.0 | 100 | +2.0 | 6/6 |
| | 0.1 | 9.0 | 100 | +3.4 | 6/6 |
| | 0.05 | 9.0 | 100 | +2.8 | 6/6 |
| | 0.025 | 9.0 | 100 | +2.4 | 6/6 |
| Control | Saline | 9.0 | — | +0.6 | 10/10 |

Tumor inoculum: $10^6$ ascites cells implanted i.p.
Host: $CDF_1$ ♀ mice.
Treatment: QD 1 → 9.
Evaluation: MST = median survival time.
Effect: % T/C = MST treated/MST control × 100.
Criteria: T/C ≧ 125 considered significant antitumor effect.

TABLE II

Effect of Compound of Example 2 on P-388 Leukemia

| Material | Dose mg/kg/day | MST Days | Effect MST % T/C | Average Weight Change,g | Survivors Day 5 |
|---|---|---|---|---|---|
| Compound of Ex. 2 | 6.4 | Tox | Tox | Tox | 2/6 |
| | 3.2 | 7.0 | 78 | −0.8 | 5/6 |
| | 1.6 | 16.0 | 178 | 0 | 6/6 |
| | 0.8 | 21.0 | 233 | +0.4 | 6/6 |
| | 0.4 | 17.0 | 189 | +0.4 | 6/6 |
| | 0.2 | 16.0 | 178 | +0.3 | 6/6 |
| | 0.1 | 13.0 | 144 | +0.8 | 6/6 |
| | 0.05 | 14.0 | 156 | +0.5 | 6/6 |
| | 0.025 | 11.0 | 122 | +0.8 | 6/6 |
| | 0.0125 | 10.0 | 111 | +0.2 | 6/6 |
| Control | Saline | 9.0 | — | 0 | 10/10 |

Tumor inoculum: $10^6$ ascites cells implanted i.p.
Host: $CDF_1$ ♀ mice.
Treatment: QD 1 → 9.
Tox: Toxicity, <4/6 survivors, Day 5.
Evaluation: MST = median survival time.
Effect: % T/C = MST treated/MST control × 100.
Criteria: T/C ≧ 125 considered significant antitumor effect.

TABLE III

Effect of Compound of Example 1 on P-388 Leukemia

| Material | Dose mg/kg/day | MST Days | Effect MST % T/C | Average Weight Change,g | Survivors Day 5 |
|---|---|---|---|---|---|
| Compound of Example 1 | 6.4 | 16.0 | 188 | +0.3 | 3/6 |
| | 3.2 | 15.0 | 176 | +0.7 | 6/6 |
| | 1.6 | 15.0 | 176 | +0.8 | 6/6 |
| | 0.8 | 13.0 | 153 | +1.6 | 6/6 |
| | 0.4 | 12.5 | 147 | +1.8 | 6/6 |
| | 0.2 | 11.0 | 129 | +1.3 | 6/6 |
| | 0.1 | 11.0 | 129 | +1.6 | 6/6 |
| | 0.05 | 10.0 | 118 | +3.1 | 6/6 |
| | 0.025 | 9.5 | 112 | +2.1 | 6/6 |
| | 0.0125 | 9.0 | 106 | +4.4 | 6/6 |
| | 0.00625 | 9.0 | 106 | +3.5 | 6/6 |
| | 0.003125 | 9.0 | 106 | +3.5 | 6/6 |
| Control | Saline | 8.5 | — | +3.1 | 10/10 |

Tumor inoculum: $10^6$ ascites cells implanted i.p.
Host: $CDF_1$ ♀ mice.
Treatment: QD 1 → 9.
Evaluation: MST = median survival time.
Effect: % T/C = MST treated/MST control × 100.
Criteria: T/C ≧ 125 considered significant antitumor effect.

TABLE IV

Effect of Compound of Example 7 on P-388 Leukemia

| Material | Dose mg/kg/day | MST Days | Effect MST % T/C | Average Weight Change,g | Survivors Day 5 |
|---|---|---|---|---|---|
| Compound of Example 7 | 1.6 | 13.0 | 144 | +0.4 | 5/6 |
| | 0.8 | 13.5 | 150 | +0.6 | 6/6 |
| | 0.4 | 11.0 | 122 | −0.3 | 6/6 |
| | 0.2 | 10.0 | 111 | +0.4 | 6/6 |
| | 0.1 | 9.0 | 100 | +0.3 | 6/6 |
| | 0.05 | 9.0 | 100 | +0.8 | 6/6 |
| | 0.025 | 9.0 | 100 | +0.8 | 6/6 |
| | 0.0125 | 9.0 | 100 | +1.0 | 6/6 |
| Control | Saline | 9.0 | — | +0.8 | 10/10 |

Tumor inoculum: $10^6$ ascitic cells implanted i.p.
Host: $CDF_1$ ♀ mice.
Treatment: QD 1 → 9.
Tox: <4/6 survivors Day 5.
Evaluation: MST = median survival time.
Effect: % T/C = (MST treated/MST control) × 100.
Criteria: % T/C ≧ 125 considered significant antitumor effect.

TABLE V

Effect of Compounds of Example 6 on P-388 Leukemia

| Material | Dose mg/kg/day | MST Days | Effect MST % T/C | Average Weight Change,g | Survivors Day 5 |
|---|---|---|---|---|---|
| Compound of Example 6 (first component) | 25.6 | 14.5 | 181 | +0.4 | 6/6 |
| | 12.8 | 13.0 | 163 | +0.8 | 6/6 |
| | 6.4 | 10.0 | 125 | 0 | 6/6 |
| Compound of Example 6 (second component) | 25.6 | 13.0 | 163 | +0.6 | 6/6 |
| | 12.8 | 10.0 | 125 | +1.2 | 6/6 |
| | 6.4 | 9.0 | 113 | +0.4 | 6/6 |
| | 3.2 | 8.0 | 100 | +0.8 | 6/6 |
| Control | Saline | 8.0 | — | −0.4 | 10/10 |

Tumor inoculum: $10^6$ ascitic cells implanted i.p.
Host: $CDF_1$ ♀ mice.
Treatment: QD 1 → 9.
Tox.: Toxicity <4/6 survivors Day 5.
Evaluation: MST = median survival time.
Effect: % T/C = MST treated/MST control × 100.
Criteria: T/C ≧ 125 considered significant antitumor effect.

TABLE VI

Effect of Compound of Example 3 on P-388 Leukemia

| Material | Dose, IP mg/kg/day | MST Days | Effect MST % T/C | Average Weight Change,g | Survivors Day 5(30) |
|---|---|---|---|---|---|
| Compound of Example 3 | 12.8 | TOX | TOX | TOX | 0/6* |
| | 6.4 | TOX | TOX | TOX | 1/6* |

TABLE VI-continued

| Effect of Compound of Example 3 on P-388 Leukemia | | | | | |
|---|---|---|---|---|---|
| Material | Dose, IP mg/kg/day | MST Days | Effect MST % T/C | Average Weight Change,g | Survivors Day 5(30) |
| | 3.2 | TOX | TOX | TOX | 3/6* |
| | 1.6 | 21.0 | 233 | −1.0 | 5/6 |
| | 0.8 | 18.0 | 200 | −0.8 | 6/6 |
| | 0.4 | 15.0 | 167 | −0.2 | 6/6 |
| | 0.2 | 13.0 | 144 | −0.1 | 5/6 |
| | 0.1 | 12.0 | 133 | +0.1 | 6/6 |

Tumor inoculum: $10^6$ ascites cells implanted i.p.
Host: $CDF_1$ ♀ mice.
Treatment: QD 1 → 9.
Tox: < 4/6 mice alive on Day 5.
Evaluation: MST = median survival time.
Effect: % T/C = (MST treated/MST control) × 100.
Criteria: % T/C ≧ 125 considered significant antitumor activity.
*Unusual eye toxicity (hemorrhage).

TABLE VII

| Effect of Compound of Example 4 on P-388 Leukemia | | | | | |
|---|---|---|---|---|---|
| Material | Dosage, IP mg/kg/day | MST Days | Effect MST % T/C | Average Weight Change,g | Survivors Day 5 |
| Compound of Example 4 | 12.8 | 19.0 | 211 | ±1.0 | 6/6 |
| | 6.4 | 20.5 | 228 | +1.2 | 6/6 |
| | 3.2 | 17.0 | 189 | +1.2 | 6/6 |
| | 1.6 | 13.0 | 144 | +0.3 | 5/6 |
| | 0.8 | 13.0 | 144 | +0.5 | 6/6 |
| | 0.4 | 10.0 | 111 | +1.3 | 6/6 |
| | 0.2 | 9.0 | 100 | +3.7 | 6/6 |
| | 0.1 | 9.0 | 100 | +3.8 | 5/6 |
| Control | Saline | 9.0 | — | +2.9 | 10/10 |

Tumor inoculum: $10^6$ ascites cells implanted i.p.
Host: $CDF_1$ ♀ mice.
Treatment: QD 1 → 9.
Evaluation: MST = median survival time.
Effect: % T/C = (MST treated/MST control) × 100.
Criteria: % T/C ≧ 125 considered significant antitumor activity.

TABLE VIII

| Effect of Compound of Example 5 on P-388 Leukemia | | | | | |
|---|---|---|---|---|---|
| Material | Dose, IP mg/kg/day | MST Days | Effect MST % T/C | Average Weight Change,g | Survivors Day 5 |
| Compound of Example 5 | 12.8 | TOX | TOX | TOX | 0/6 |
| | 6.4 | TOX | TOX | TOX | 0/6 |
| | 3.2 | TOX | TOX | TOX | 1/6 |
| | 1.6 | 19.0 | 211 | −1.6 | 5/6 |
| | 0.8 | 19.0 | 211 | −0.4 | 6/6 |
| | 0.4 | 16.0 | 178 | +0.3 | 6/6 |
| | 0.2 | 15.0 | 167 | −0.4 | 6/6 |
| | 0.1 | 12.0 | 133 | +0.4 | 6/6 |
| Control | Saline | 9.0 | — | +0.8 | 10/10 |

Tumor inoculum: $10^6$ ascites cells implanted i.p.
Host: $CDF_1$ ♀ mice.
Treatment: QD 1 → 9.
Evaluation: MST = median survival time.
Effect: % T/C = (MST treated/MST control) × 100.
Criteria: % T/C ≧ 125 considered significant antitumor activity.

TABLE IX

| Effect of Compounds of Examples 4 and 5 on L1210 Leukemia | | | | | |
|---|---|---|---|---|---|
| Material | Dose, IP mg/kg/day | MST Days | Effect MST % T/C | Average Weight Change,g | Survivors Day 5(30) |
| Compound of Example 4 | 12.8 | 11.0 | 183 | +0.3 | 6/6 |
| | 9.6 | 12.0 | 200 | +0.3 | 6/6 |
| | 6.4 | 12.0 | 200 | +0.2 | 5/5 |
| | 3.2 | 7.0 | 117 | +1.9 | 6/6 |
| | 1.6 | 9.0 | 150 | +0.2 | 6/6 |
| | 0.8 | 7.5 | 125 | +0.8 | 6/6 |
| Compound of Example 5 | 2.4 | 11.0 | 183 | −1.3 | 6/6 |
| | 2.0 | 10.0 | 167 | −1.2 | 6/6 |
| | 1.6 | 10.5 | 175 | −0.4 | 6/6 |

TABLE IX-continued

| Effect of Compounds of Examples 4 and 5 on L1210 Leukemia | | | | | |
|---|---|---|---|---|---|
| Material | Dose, IP mg/kg/day | MST Days | Effect MST % T/C | Average Weight Change,g | Survivors Day 5(30) |
| | 1.2 | 10.0 | 167 | −0.3 | 6/6 |
| | 0.8 | 9.0 | 150 | −0.2 | 6/6 |
| | 0.4 | 8.5 | 142 | +0.3 | 6/6 |
| | 0.2 | 7.0 | 117 | +1.3 | 6/6 |
| | 0.1 | 7.0 | 117 | +1.3 | 6/6 |
| Control | Saline | 6.0 | — | +2.6 | 10/10 |

Tumor inoculum: $10^6$ ascites cells implanted, i.p.
Host: $BDF_1$ ♀ mice.
Treatment: QD 1 → 9.
Evaluation: MST = median survival time.
Effect: % T/C = (MST treated/MST control). × 100
Criteria: % T/C ≧ 125 considered significant antitumor activity.

TABLE X

| Effect of Compound of Example 3 on L1210 Leukemia | | | | | |
|---|---|---|---|---|---|
| Material | Dose, IP mg/kg/inj | MST Days | Effect MST % T/C | Average Weight Change,g | Survivors Day 5(30) |
| Compound of Example 3 | 2.4 | 10.5 | 162 | −0.7 | 6/6 |
| | 2.0 | 10.0 | 154 | −0.6 | 6/6 |
| | 1.6 | 10.5 | 162 | −1.3 | 6/6 |
| | 1.2 | 10.0 | 154 | −0.7 | 6/6 |
| | 0.8 | 9.0 | 138 | −0.4 | 6/6 |
| | 0.4 | 9.5 | 146 | −0.9 | 6/6 |
| Control | Saline | 6.5 | — | +4.0 | 10/10 |

Tumor inoculum: $10^6$ ascites cells implanted i.p.
Host: $CDF_1$ ♂ mice.
Treatment: QD 1 → 9.
Evaluation: MST = median survival time.
Effect: % T/C = (MST treated/MST control) × 100.
% T/C ≧ 125 considered significant antitumor activity.

TABLE XI

| Effect of Compound of Example 3 on Lewis Lung Carcinoma | | | | | |
|---|---|---|---|---|---|
| Material | Dose, IP mg/kg/day | MST Days | Effect MST % T/C | Average Weight Change | Survivors Day 5(60) |
| Compound of Example 3 | 2.0 | 23.0 | 135 | −0.2 | 10/10 |
| | 1.5 | 26.5 | 156 | −0.1 | 10/10 |
| | 1.0 | 21.5 | 126 | +0.5 | 10/10 |
| | 0.5 | 18.5 | 109 | −0.6 | 10/10 |
| Control | Saline | 17.0 | — | −0.6 | 10/10 |

Tumor inoculum: $10^6$ tumor brei cells, ip.
Host: $BDF_1$ ♂ mice.
Treatment: QD 1 → 9.
Tox: < 6/10 mice alive on Day 5.
Evaluation: MST = median survival time.
Effect: % T/C = (MST treated/MST control) × 100.
Criteria: % T/C ≧ 125 considered significant antitumor activity.

The experimental animal tests described above demonstrate that the compounds of the present invention possess marked inhibitory action against mammalian malignant tumors.

According to another aspect of this invention, therefore, there is provided a method for therapeutically treating a mammalian host affected by a malignant tumor which comprises administering to said host an effective tumor-inhibiting dose of a compound of formula I–V.

In yet another aspect of this invention, a pharmaceutical composition is provided which comprises an effective tumor-inhibiting amount of a compound of formula I–V in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred dosages of the compounds of the present invention will vary according to the particular compound being used, the particular composition formulated, the mode of administration and the particular situs, host and disease being treated. Many factors that modify the action of the drug will be taken into account by those skilled in the art, e.g. age, body weight, sex, diet, time of administration, route of administration, rate of excretion, condition of the host, drug combinations, reaction sensitivities and severity of the disease. Optimal dosages for a given set of conditions can be ascertained by those skilled in the art using conventional dosage determination tests in view of the experimental animal data provided, the available data on clinical use of anguidine and the above-mentioned guidelines.

The following examples are not limiting but are intended to be illustrative of this invention. SKELLYSOLVE B is a commercially available petroleum solvent (Skelly Oil Co.) comprising isomeric hexanes and having a boiling point of 60°-68° C. The main component of SKELLYSOLVE B is n-hexane. Unless otherwise indicated, all melting points below are uncorrected, all temperatures are in degrees Celsius and all solvent percentages are by volume. The silica gel used in the examples (unless otherwise indicated) is SILICAR CC-7 (trademark of Mallinckrodt Chemical Works).

PREPARATION OF STARTING MATERIALS

Preparation 1

4β,15-Diacetoxy-3α-0-(2'-tetrahydropyranyl)-12,13-epoxytrichlothec-9-ene

A mixture of 4β,15-diacetoxy-3α-hydroxy-12,13-epoxytrichothec-9-ene (12.81 g, 35 mmol), 2,3-dihydro-4H-pyran (17.5 ml, 189 mmol), and p-toluenesulfonic acid (70 mg, 0.35 mmol) in 150 ml of $CH_2Cl_2$ was stirred at room temperature for 2 h. After addition of 2.1 g of $K_2CO_3$, the reaction mixture was diluted with 400 ml of $CH_2Cl_2$ and washed with saturated $NaHCO_3$ solution and brine. Drying over $K_2CO_3$ and removal of the solvent gave a colorless oil which crystallized slowly from petroleum ether to give 11.30 g (72%) of solid. m.p. 93°-94° C.; IR(KBr): 2976, 1746, 1249, 1080, 1040, 988 $cm^{-1}$.

Anal. Calc'd for $C_{24}H_{34}O_8$: C, 63.98; H, 7.61. Found: C, 64.35; H, 7.58.

PREPARATION 2

3α,4β,15-Trihydroxy-12,13-epoxytrichothec-9-ene

4β,15-Diacetoxy-3α-hydroxy-12,13-epoxytrichothec-9-ene (15 g) was stirred for 20 minutes in 300 ml of methanol with 900 ml of 0.3 N sodium hydroxide (Sigg et al. Helv. Chim. Acta, 48, 962-988 (1965). The solution was placed on a column containing 1 kg of DOWEX 50 ($H^+$ cycle) prepared with 20% methanol in water. The column was eluted with 3 l of the same solvent, the eluate concentrated, and the residual aqueous solution freeze-dried. The powder was dissolved in methanol, mixed with 10 g of silica gel, and dried in vacuo. The dry silica gel mixture was placed on a column of fresh silica gel (2.5×100 cm) and eluted with methylene chloride with increasing amounts of methanol. Fractions appearing homogeneous on TLC plates were dried and crystallized from ethyl acetate. Yield: 7.3 g, m.p. 194°-195° C. IR(KBr): 3490, 3450, 3390, 2990-2900 (four peaks), 1675, 960 and 950 $cm^{-1}$. $[\alpha]_D^{22} = -15.4°$ (c=1, acetone).

Anal. Calc'd for $C_{15}H_{22}O_6$: C, 63.81; H, 7.86. Found: C, 63.71; H, 7.80.

Alternatively, the 3-0-tetrahydropyranyl derivative (Preparation 3 below (1 g) was stirred for four hours in 115 ml of 95% ethanol and 23 ml of 1 N HCl. The solution was azeotropically distilled with the addition of absolute ethanol, the concentrated ethanolic solution diluted with diethyl ether, and the resulting title product separated from ethyl acetate as a gum.

PREPARATION 3

4β,15-Dihydroxy-3α-0-(2'-tetrahydropyranyl)-12,13-epoxytrichothec-9-ene

To a solution of 4β,15-diacetoxy-3-0-(2'-tetrahydropyranyl)-12,13-epoxytrichothec-9-ene (1.067 g, 2.37 mmol) in 40 ml of tetrahydrofuran and methanol (5:3 v/v) was added 20 ml of 0.3 N NaOH solution. After 2.5 h of stirring at room temperature, an additional 20 ml of 0.3 N NaOH solution was introduced, and stirring was continued for 18.5 h. The resulting solution was diluted with $CH_2Cl_2$ (200 ml) and washed with water. The aqueous layer was reextracted with $CH_2Cl_2$ (2×50 ml). The combined $CH_2Cl_2$ layers were washed with brine and dried over $K_2CO_3$. Removal of the solvent gave 891 mg of foam, which was subsequently chromatographed on silica gel. Elution with 1% methanol-$CH_2Cl_2$ gave 46 mg (5%) of 15-acetoxy-4β-hydroxy-3α-0-(2'-tetrahydropyranyl)-12,13-epoxytrichothec-9-ene. A further elution with 5% methanol-$CH_2Cl_2$ gave 808 mg (93%) of the title compound as an amorphous solid. IR(KBr): 3457, 2943, 1445, 1135, 1125, 1078, 1035, 1020, 978, 957 $cm^{-1}$.

PREPARATION 4

15-Acetoxy-4β-hydroxy-3α-0-(2'-tetrahydropyranyl)-12,13-epoxytrichothec-9-ene

To a solution of 4β,15-diacetoxy-3α-0-(2'-tetrahydropyranyl)-12,13-epoxytrichothec-9-ene (31.14 g, 69.2 mmol) in 800 ml of methanol and tetrahydrofuran (1:1 v/v) was added 400 ml of 1.31 N $NH_4OH$ solution. After 3 days stirring at room temperature, 10 ml of concentrated $NH_4OH$ solution was added to the reaction mixture. Stirring was continued for an additional 4 days. The volume of the resulting solution was reduced to 500 ml. Extraction with $CH_2Cl_2$, washing with brine, and removal of the solvent gave 37 g of a slightly yellow oil. Chromatography on silica gel (elution with 1% methanol-$CH_2Cl_2$) gave 10.65 g (38%) of the title compound as an oil. The NMR and IR spectra of this material were consistent with the structure of the title compound. IR(KBr): 3430, 2970, 2950, 2875, 1744, 1720, 1270, 1248, 1126, 1080, 1040, 972 $cm^{-1}$.

PREPARATION 5

4β,15-Bis-(bromoacetoxy)-3α-hydroxy-12,13-epoxytrichothec-9-ene

A solution containing 183 mg (0.5 mmol) of 3α-0-(2'-tetrahydropyranyl)-4β,15-dihydroxy-12,13-epoxytrichothec-9-ene and 268 mg (2.5 mmol) of 2,6-lutidine was cooled to 5° C. To this solution was added with stirring 253 mg (1.25 mmol) of bromoacetyl bromide and the resulting solution was kept without cooling for 18 h. The usual work-up gave a gum which was dissolved in 36 ml of 95% ethanol and 6 ml of 1 N HCl and stored for 20 h at 22° C. The usual work-up gave a foam which was chromatographed on 20 g of silica gel (Mallinckrodt SILICAR CC-7) using 1% methanol in $CH_2Cl_2$ as the solvent. The product eluted as a pale yellow band which gave a foam on evaporation of the solvent. Crystalllization from diethyl ether afforded a colorless solid of m.p. 125°–126°. IR(KBr): 3480, 2960, 1750, 1735, 1280, 1165 cm−.

Anal. Calc'd for $C_{19}H_{24}Br_2O_7$: C, 43.53; H, 4.61. Found: C, 45.47; H, 4.84.

PREPARATION 6

4β,15-Bis(chloroacetoxy)-3α-0-(2'-tetrahydropyranyl)-12,13-epoxytrichothec-9-ene A mixture of 4β,15-dihydroxy-3α-0-(2'-tetrahydropyranyl)-12,13-epoxytrichothec-9-ene (808 mg, 2.21 mmol), chloroacetic anhydride (1.132 g, 6.62 mmol) and pyridine (894 mg, 11.05 mmol) in 100 ml of $CH_2Cl_2$ was stirred at room temperature for 14 h. The reaction mixture was diluted with 200 ml of $CH_2Cl_2$ and washed with saturated $NaHCO_3$ solution, 1% HCl solution and brine. Drying over $K_2CO_3$ and removal of the solvent gave 1.058 g (92%) of foam which was homogeneous on TLC. A portion of this material was purified by silica gel chromatography (elution with 0.5% methanol-$CH_2Cl_2$) to furnish an analytical sample of title product. IR(KBr): 2955, 1762, 1740, 1290, 1186, 1172, 1129, 1080, 1039, 977 $cm^{-1}$.

PREPARATION 7

4β,15-Bis(chloroacetoxy)-3α-hydroxy-12,13-epoxytrichothec-9-ene

To a solution of 4β,15-bis(chloroacetoxy)-3α-0-(2'-tetrahydropyranyl)-12,13-epoxytrichothec-9-ene (858 mg, 1.65 mmol) in 100 ml of 95% ethanol was added 19 ml of 1 N HCl solution. The resulting solution was stirred at room temperature for 24 hours. The reaction mixture was diluted with $CH_2Cl_2$ (300 ml) and washed with saturated $NaHCO_3$ solution and brine. Drying over $K_2CO_3$-$Na_2SO_4$ and removal of the solvent gave 600 mg of foam. Chromatography of this material on silica gel (elution with 1% methanol-$CH_2Cl_2$) gave 524 mg (73%) of 4β,15-bis(chloroacetoxy)-3α-hydroxy-12,13-epoxytrichothec-9-ene. An analytical sample was obtained by recrystallization from chloroform-diethyl ether, m.p. 139°–141° C. IR(KBr): 3450, 2970, 2913, 1758, 1742, 1327, 1293, 1192, 1173, 1083, 1008, 967 $cm^{-1}$. Elution of the silica gel column with 2% methanol-$CH_2Cl_2$ gave 110 mg (15%) of 15-chloroacetoxy-3α,4β-dihydroxy-12,13-epoxytrichothec-9-ene.

Anal. Calc'd. for $C_{19}H_{24}O_7Cl_2$: C, 52.42; H, 5.56. Found: C, 52.31; H, 5.34.

PREPARATION 8

15-Acetoxy-4β-chloroacetoxy-3α-hydroxy-12,13-epoxytrichothec-9-ene

A mixture of 15-acetoxy-4β-hydroxy-3α-O-(2'-tetrahydropyranyl)-12,13-epoxytrichothec-9-ene (785 mg, 1.92 mmol), chloroacetic anhydride (492 mg, 2.88 mmol) and pyridine (0.309 ml, 3.84 mmol) in 100 ml of $CH_2Cl_2$ was stirred at room temperature for 28.5 h. The reaction mixture was diluted with $CH_2Cl_2$ (200 ml) and washed with saturated $NaHCO_3$ solution and brine. Drying over $K_2CO_3$ and removal of the solvent gave 931 mg (100%) of a white foam. The NMR and IR spectra of this material were consistent with the structure of 15-acetoxy-4β-chloroacetoxy-3α-O-(2'-tetrahydropyranyl)-12,13-epoxytrichothec-9-ene.

To a solution of 15-acetoxy-4β-chloroacetoxy-3α-O-(2'-tetrahydropyranyl)-12,13-epoxytrichothec-9-ene (900 mg, 1.98 mmol) in 100 ml of 95% ethanol was added 19 ml of 1 N HCl solution. After 10 h of stirring at room temperature, 200 ml of $CH_2Cl_2$ was added to the reaction mixture. The aqueous layer which separated was extracted with 25 ml of $CH_2Cl_2$. The combined $CH_2Cl_2$ layers were washed with saturated $NaHCO_3$ solution and brine. Drying over $K_2CO_3$—$Na_2SO_4$ and removal of the solvent gave 662 mg of foam. Chromatography on silica gel (elution with 0.5% methanol-$CH_2Cl_2$) gave 350 mg (44%) of the title compound. Recrystallization from diethyl ether furnished the analytical sample; m.p. 166°–167.5° C. IR(KBr): 3500, 3040, 3020, 2989, 2918, 1754, 1736, 1378, 1330, 1260, 1208, 1167, 1074, 1052, 960 $cm^{-1}$.

Anal. Calc'd for $C_{19}H_{25}O_7Cl$: C, 56.83; H, 6.29. Found: C, 57.12; H, 6.29.

PREPARATION 9

15-(trans-2'-Butenoyloxy)-3α,4β-dihydroxy-12,13-epoxytrichothec-9-ene

A solution containing 366 mg (1 mmol) of 3α-O-(2'-tetrahydropyranyl)-4β,15α-dihydroxy-12,13-epoxytrichothec-9-ene and 395 mg (5 mmol) of dry pyridine in 50 ml of $CH_2Cl_2$ (previously dried over 4 Å molecular sieves) was cooled at 5° C. To the stirred solution was added dropwise 261 mg (2.5 mmol) of trans-2-butenoic acid chloride and, after completion of the addition, the mixture was stirred for 1 h at 5° C. and for 16 h at ambient temperature. The solution was diluted with 50 ml of $CH_2Cl_2$ and was successively washed with saturated aqueous $NaHCO_3$, brine, 1% aqueous HCl and brine. The organic phase was dried over $Na_2SO_4$ and the solvent was evaporated under reduced pressure to provide 360 mg of a gum. This was dissolved in 50 ml of 95% ethanol and to it was added 5 ml of 2 N HCl. After the solution had been stored at room temperature for 22 h, it was diluted with 100 ml of $CH_2Cl_2$ and was washed successively with $H_2O$, saturated aqueous $NaHCO_3$ and brine. The organic phase was dried over $Na_2SO_4$ and the solvent was evaporated under reduced pressure to provide 260 mg of gum. This was chromatographed on 20 g of silica gel using 1% methanol in $CH_2Cl_2$ as the solvent. The first product eluted was the bis-ester (26 mg) (Preparation 10) followed by 22 mg of the 4-monoester (Preparation 10) and then 147 mg of the title compound which was crystallized from $CHCl_3$—SKELLYSOLVE B as a white solid of m.p. 83°–86° C. IR(KBr): 3440, 2970, 1725, 1190, 1110, 1085, 965 $cm^{-1}$.

Anal. Calc'd for $C_{19}H_{26}O_6.0.5H_2O$: C, 63.49; H, 7.57. Found: C, 63.54; H, 7.43.

PREPARATION 10

4β,15-Bis-(trans-2'-butenoyloxy)-3α-hydroxy-12,13-epoxytrichothec-9-ene

Repetition of the above experiment using 6 equivalents of trans-2-butenoic acid chloride gave the title compound as a hygroscopic white foam. IR(KBr): 3420, 2970, 1720, 1310, 1260, 1185, 965 $cm^{-1}$. In addition, there was obtained 4β(trans-2'-butenoyloxy)-3α,15- dihydroxy-12,13-epoxytrichothec-9-ene as a cream solid of m.p. 60°-62° C. IR(KBr): 3460, 2960, 1710, 1315, 1190, 1105, 1080, 955 $cm^{-1}$.

Anal. Calcd for $C_{19}H_{26}O_6.0.25H_2O$: C, 64.30; H, 7.53. Found: C, 64.19; H, 8.06.

PREPARATION 11

15-(2'-Methylpropenoyloxy)-3α,4β-dihydroxy-12,13-epoxytrichothec-9-ene

To a solution of 366 mg (1 mmol) of 3α-O-(2'-tetrahydropyranyl)-4β,15-dihydroxy-12,13-epoxytrichothec-9-ene and 395 mg (5 mmol) of dry pyridine in 50 ml of methylene chloride (dried over 4 Å molecular sieves) was added with stirring 261 mg (2.5 mmol) of freshly distilled 2-methylpropenoic acid chloride. The solution was stored at 22° C. for 17 h and was then treated with an additional 261 mg (2.5 mmol) of the acid chloride. After a further 22 h at 22° C., the solution was worked up as described in Preparation b 9 before hydrolysis and the residue was chromatographed on 20 g of silica gel. 2-Methylpropenoic acid anhydride was eluted using 1% methanol in $CH_2Cl_2$. The solvent was changed to methanol to elute 230 mg of white foam which was hydrolyzed as described above (Preparation 9) to give 189 mg of a foam. This was chromatographed on 20 g silica gel using 1% methanol in $CH_2Cl_2$ as the solvent. Minor products were eluted and the solvent was changed to 20% methanol in $CH_2Cl_2$ to afford 116 mg (33%) of the title compound as a foam which crystallized from $CH_2Cl_2$—SKELLYSOLVE B as a pale pink solid of m.p. 79°-81° C. IR(KBr): 3440, 2960, 1715, 1165, 1080, 955 $cm^{-1}$.

Anal. Calc'd for $C_{19}H_{26}O_6.0.5H_2O$: C, 63.49; H, 7.57. Found: C, 63.36; H, 7.40.

PREPARATION 12

4β,15-Bis-(2'-methylpropenoyloxy)-3α-hydroxy-12,13-epoxytrichothec-9-ene

A solution containing 3.66 g (0.01 mol) of 3α-O-(2'-tetrahydropyranyl)-4β,15-dihydroxy-12,13-epoxytrichothec-9-ene, 3.95 g (0.05 mol) of pyridine and 2.61 g (0.025 mol) of freshly distilled 2-methylpropenoic acid chloride in 250 ml of dry methylene chloride was stirred for 16 h at 22° C. An additional 2.61 g (0.025 mol) of the acid chloride was added and stirring was continued for 6 h. The solution was diluted with $CH_2Cl_2$ and was washed in succession with saturated aqueous $NaHCO_3$, brine, 1% aqueous HCl and brine. The organic phase was dried over $Na_2SO_4$ and the solvent evaporated under reduced pressure to give 5.36 g of an oil. This was chromatographed on 100 g of silica gel using 1% methanol in $CH_2Cl_2$ as the solvent. Methacrylyl anhydride was first eluted, followed by 615 mg of a foam which was hydrolysed as before (Preparation 9) in 67.5 ml of 95% ethanol and 13.5 ml of 1 N HCl. The usual work-up gave 590 mg of gum from which, by chromatography, 198 mg of the title compound was isolated as a hygroscopic foam IR(KBr): 3500, 2960, 1720, 1165, 1080, 960 $cm^{-1}$; which was identified by its NMR spectrum. The next fraction from this chromatography afforded 4β-(2'-methylpropenoyloxy)-3α,15-dihydroxy-12,13-epoxytrichothec-9-ene as colorless crystals of m.p. 175°-176° C. IR(KBr): 3510, 3460, 2500, 1690, 1330, 1300, 1170, 1080, 1060, 910, 900 $cm^{-1}$.

Anal. Calc'd for $C_{19}H_{26}O_6.0.25H_2O$: C, 64.30; H, 7.53. Found: C, 64.24; H, 7.14.

From the chromatographic separation of the tetrahydropyranyl ethers (above) there was next obtained 810 mg of a foam which was re-chromatographed on fresh silica gel (20 g) using the same solvent system to provide 3α-O-(2'-tetrahydropyranyl)-15-(2'-methylpropenoyloxy)-4β-hydroxy-12,13-epoxytrichothec-9-ene as a foam.

PREPARATION 13

4β-(Chloroacetoxy)-15-(2'-methylpropenoyloxy)-3α-hydroxy-12,13-epoxytrichothec-9-ene To a stirred solution of 164 mg (0.38 mmol) of 3α-O-(2'-tetrahydropyranyl)-15-(2'-methylpropenoyloxy)-4β-hydroxy-12,13-epoxytrichothec-9-ene (Preparation 12) in 25 ml of dry $CH_2Cl_2$ were added in succession 36 mg (0.46 mmol) of pyridine and 78 mg (0.46 mmol) of chloroacetic anhydride. The solution was stored for 17 h at 22° C. The solution was worked up as before and hydrolysed as usual with 27 ml of 95% ethanol and 5.4 ml of 1 N HCl. After work-up as before there was obtained a gum which was triturated with SKELLYSOLVE B to provide a hydroscopic solid of m.p. 58°-60° C. IR(KBr): 2960, 1755, 1715, 1320, 1295, 1165, 1085, 955 $cm^{-1}$.

Anal. Calc'd for $C_{21}H_{27}ClO_7$: C, 59.08; H, 6.38. Found: C, 60.48; H, 6.66.

PREPARATION 14

Following the general procedure of Preparation 5 with the bromoacetyl bromide used therein replaced by an equimolar weight of the appropriate acylating agent, the following compounds were prepared:

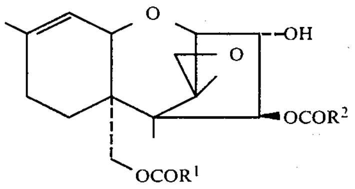

| $R^1$ | $R^2$ |
|---|---|
| $-CH_2CH_3$ | $-CH_2CH_3$ |
| $-CH_2CH_2CH_3$ | $-CH_2CH_2CH_3$ |
| $-CH_2CH_2CH_2CH_3$ | $-CH_2CH_2CH_2CH_3$ |
| 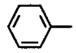 | 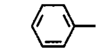 |

PREPARATION 15

If the general procedure of Preparations 6-7 is repeated with the chloroacetic anhydride used therein replaced by an equimolar amount of the appropriate acylating agent, the following esters may be obtained.

Product

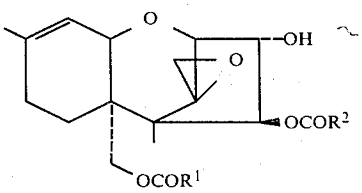

| Acylating Agent | $R^1$ | $R^2$ |
|---|---|---|
| trifluoroacetic anhydride | $-CF_3$ | $-CF_3$ |

-continued

| Acylating Agent | $R^1$ | $R^2$ |
|---|---|---|
| Product | 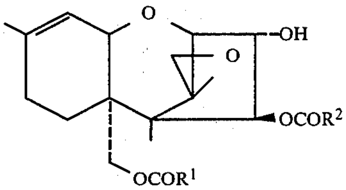 | |
| isobutyryl chloride | $-CH(CH_3)_2$ | $-CH(CH_3)_2$ |
| valeryl chloride | $-(CH_2)_3CH_3$ | $-(CH_2)_3CH_3$ |
| m-toluoyl chloride | 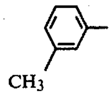 | 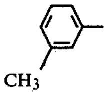 |
| p-anisoyl chloride | 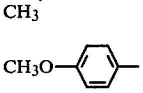 | 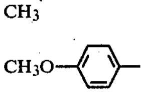 |
| p-chlorobenzoyl chloride | 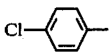 | 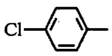 |
| phenylacetyl chloride | 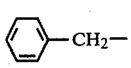 | 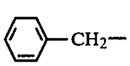 |

PREPARATION 16

If the general procedure of Preparation 8 is repeated with the chloroacetic anhydride used therein replaced with an equimolar amount of the acylating agents listed in Preparation 15, the following mixed esters may be obtained.

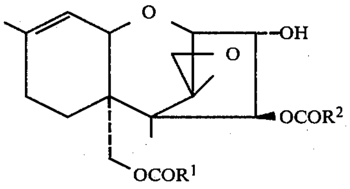

| $R^1$ | $R^2$ |
|---|---|
| $-CH_3$ | $-CF_3$ |
| $-CH_3$ | $-CH(CH_3)_2$ |
| $-CH_3$ | $-(CH_2)_3CH_3$ |
| $-CH_3$ | 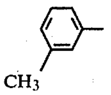 |
| $-CH_3$ | 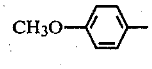 |
| $-CH_3$ | 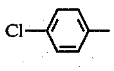 |
| $-CH_3$ | 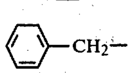 |

PREPARATION 17

Esters of the type

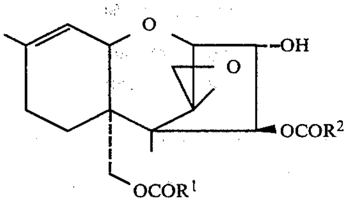

where $R^1 \neq R^2$ may be prepared by a procedure similar to that used for Preparation 13. By using less than two equivalents of an acylating agent listed in Preparation 15, a mixture of monoacylated products of the formulae

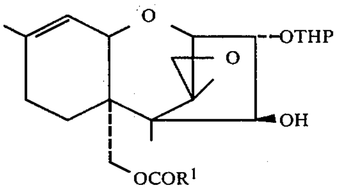

and

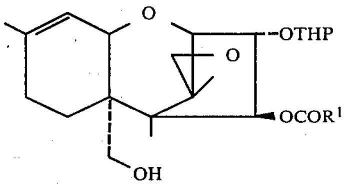

are produced. These products may be separated chromatographically and then treated with a second acylating agent selected from the list provided in Preparation 15 (the second reagent being different than the first) to give products such as shown below.

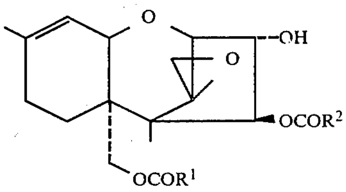

| $R^1$ | $R^2$ |
|---|---|
| $-CF_3$ | 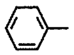 |
| $-CF_3$ | $-CH(CH_3)_2$ |
| 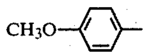 | $-(CH_2)_3CH_3$ |
| 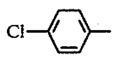 | 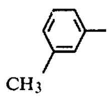 |
| $-CH(CH_3)_2$ | 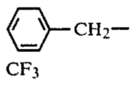 |
| 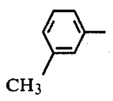 | |

PREPARATION 18

Following the general procedures illustrated above, the following esters may be prepared.

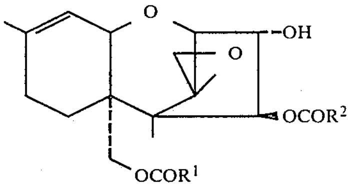

| $R^1$ | $R^2$ |
|---|---|
| $-CH_3$ | $-C=CH_2$<br>\|<br>$CH_3$ |
| $-C=CH_2$<br>\|<br>$CH_3$ | $-C=CH_2$<br>\|<br>$CH_3$ |
| $-C=CH_2$<br>\|<br>$CH_3$ | $-CH_2Cl$ |
| $-CH=CH$<br>\|<br>$CH_3$ | $-CH=CH$<br>\|<br>$CH_3$ |
| $-CH_2Cl$ | $-C=CH_2$<br>\|<br>$CH_3$ |
| $-CH_2CH_2CHClCH_3$ | $-CH_2CH_2CHClCH_3$ |
| $-CH_2CHClCH_3$ | $-CH_2CHClCH_3$ |
| $-CH_2CHCH_3$<br>\|<br>$CH_2Cl$ | $CH_2CHCH_3$<br>\|<br>$CH_2Cl$ |
| $-CCl_3$ | $-CCl_3$ |
| $-CF_3$ | 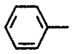 |
| $-CH_3$ | 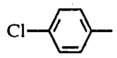 |
| $(CH_3)_2CH-$ | $-CH_2Cl$ |
| 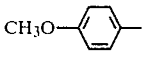 | $-CH_2CH_2CH_3$ |
| 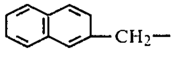 | 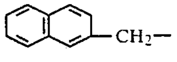 |
| 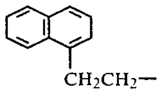 | 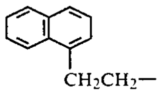 |
| 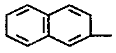 | 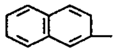 |
| 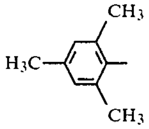 | 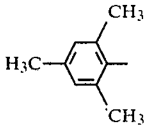 |
| 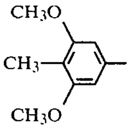 | 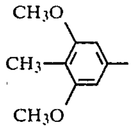 |
| $-CH=CH_2$ | $-CH=CH_2$ |
| $-C=CH_2$<br>\|<br>$CH_2Br$ | $-C=CH_2$<br>\|<br>$CH_2Br$ |
| $-C\equiv CCH_3$ | $-C\equiv CCH_3$ |
| $-C\equiv CH$ | $-C\equiv CH$ |

-continued

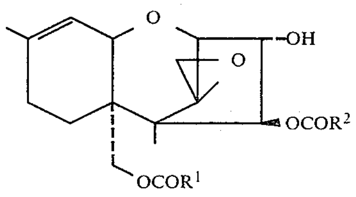

| $R^1$ | $R^2$ |
|---|---|
| 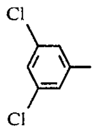 | 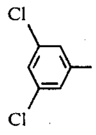 |
| 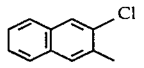 | 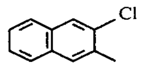 |
| 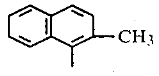 | 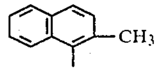 |
| 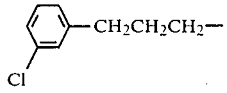 | 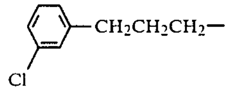 |
| 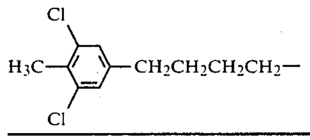 | $-CH_2Cl$ |

PREPARATION 19

4β,15-Diacetoxy-12,13-epoxytrichothec-9-en-3-one

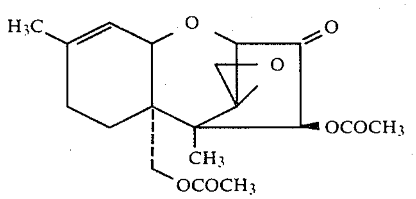

The title compound has been reported as a minor (17%) product in the $CrO_3$ oxidation of 4β,15-diacetoxy-3α-hydroxy-trichothec-9-ene.[1] A new procedure similar to that described for 4β,15-dichloroacetoxy-12,13-epoxytrichothec-9-en-3-one (Example 1) provided the title compound in 82% yield from the same starting material. Recrystallization from diethyl ether furnished an analytical sample: mp 160°-161° (lit.[1] 161°-162°); IR (KBr): 2995, 2930, 2883, 1766, 1740, 1388, 1365, 1240, 1220, 1112, 1045, 1017, 948, 926 $cm^{-1}$.

1. H. P. Sigg et al., *Helv. Chim. Acta*, 48, 962 (1965).

EXAMPLE 1

4β,15-Dichloroacetoxy-12,13-epoxytrichothec-9-en-3-one

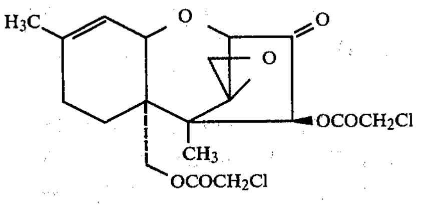

To a solution of 70 mg (0.90 mmol) of dimethyl sulfoxide in 3 ml of dry $CH_2Cl_2$ was added at −78° a 10% $CH_2Cl_2$ solution of trifluoroacetic anhydride (0.45 mmol). After 10 min of stirring at −78°, a solution of 4β,15-dichloroacetoxy-3α-hydroxy-12,13-epoxytrichothec-9-ene (130 mg, 0.299 mmol) in 3 ml of $CH_2Cl_2$ was added dropwise. Stirring was continued for 30 min, and then triethylamine (88 mg, 0.87 mmol) was added. After an additional 10 min at −78°, the reaction mixture was warmed to room temperature. It was diluted with $CH_2Cl_2$ (100 ml) and washed with water. Drying over $Na_2SO_4$ and removal of the solvent gave 143 mg of oil. This material was dissolved in diethyl ether and precipitated with hexane to give 120 mg (93%) of title product as a white powder. The NMR and IR spectra were consistent with the structure: IR(KBr): 2967, 2913, 1773 (sh), 1760, 1745 (sh), 1316, 1340, 1307, 1170, 1165, 1052, 1008, 962, 930 $cm^{-1}$.

EXAMPLE 2

15-Acetoxy-4β-chloroacetoxy-12,13-epoxytrichothec-9-en-3-one

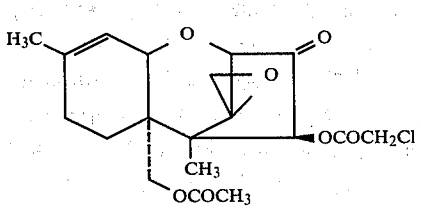

The title compound was prepared analogously to 4β,15-dichloroacetoxy-12,13-epoxytrichothec-9-en-3-one (Example 1) starting with 15-acetoxy-4β-chloroacetoxy-3α-hydroxy-12,13-epoxytrichothec-9-ene. Recrystallization of the product from diethyl ether and hexane gave an analytical sample in 49% yield: mp 154°-155.5°; IR (KBr): 3020, 2984, 2970, 2916, 1776, 1734, 1280, 1258, 1242, 1052 $cm^{-1}$.

Anal. Calc'd. for $C_{19}H_{23}O_7Cl$: C, 57.21; H, 5.81. Found: C, 57.41; H, 5.78.

EXAMPLE 3

4β,15-Bismethacryloyloxy-12,13-epoxytrichothec-9-en-3-one

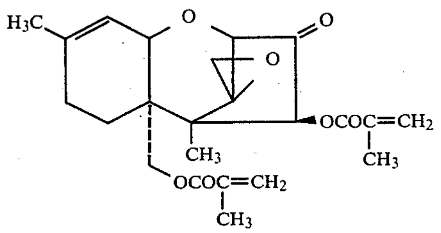

Following the procedures of Examples 1 and 2, 4β,15-bismethacryloyloxy-3α-hydroxy-12,13-epoxytrichothec-9-ene was oxidized to the title compound. The crude reaction product was extracted with hot Skellysolve B and on cooling, the solution deposited a gum which could not be crystallized. The NMR spectrum of this gum was consistent with the proposed structure. IR (KBr): 2960, 1770, 1725, 1160, 1060, 960, 950 $cm^{-1}$.

EXAMPLE 4

2'-Methyl-5'αH-15-acetoxy-3α-hydroxy-12,13-epoxytrichotheceno-[3,4-d]oxazole

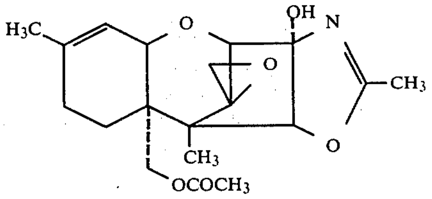

Sodium cyanoborohydride (1.56 g, 24.8 mmol) was added to a solution of 4β,15-diacetoxy-12,13-epoxytrichothec-9-en-3-one (9.03 g, 24.8 mmol) and ammonium acetate (19.25 g, 250 mmol) in 400 ml of methanol. After 22 hr. of stirring at room temperature, approximately 20 g of 3 A molecular sieves were added. The reaction mixture was further stirred at room temperature for 20 hr., and then filtered and concentrated to 100 ml. The resulting solution was diluted with 500 ml of $CH_2Cl_2$ and washed with water and brine. The combined aqueous layers were re-extracted with $CH_2Cl_2$. The $CH_2Cl_2$ layers were combined and dried over $Na_2SO_4$. The foam obtained after evaporation of the solvent was crystallized from diethyl ether to give 4.86 g of colorless crystals. Addition of Skellysolve B to the mother liquor gave an additional 3.20 g of crystals: total 8.06 g (90%), mp 136°-140°; IR (KBr): 3350, 2960, 1742, 1665, 1432, 1371, 1335, 1238, 1175, 1125, 1073, 1040, 1020, 990, 960, 920 $cm^{-1}$.

Anal. Calc'd. for $C_{19}H_{25}NO_6$: C, 62.79; H, 6.93; N, 3.85. Found: C, 62.76; H, 6.92; N, 3.78.

EXAMPLE 5

4β-Chloroacetoxy-15-methacryloyloxy-12,13-epoxytrichothec-9-en-3-one

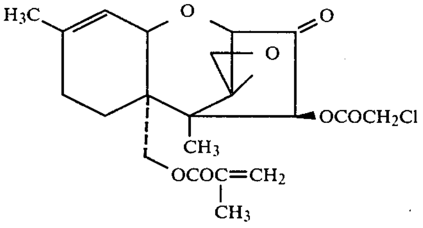

To a stirred solution of 98 mg (1.25 mmol) of dry dimethylsulfoxide in 3 ml of dry methylene chloride at −78° under a nitrogen atmosphere was added 158 mg (0.75 mmol) of trifluoroacetic anhydride. After 10 min. a solution of 213 mg (0.5 mmol) of 4β-chloroacetoxy-15-methacryloyloxy-3α-hydroxy-12,13-epoxytrichothec-9-ene in 3 ml of methylene chloride was added. The reaction mixture was stirred under nitrogen for 1¼ hr. at −50° to −55°. Triethylamine (126 mg, 1.25 mmol) was added and after 10 min. the reaction was allowed to attain room temperature. The solution was diluted with methylene chloride and washed with water and with brine. The organic phase was dried over anhydrous sodium sulfate and the solvent removed under reduced pressure to afford 205 mg of white foam whose infrared and NMR spectra were consistent with the title structure. IR(KBr): 2970, 1775, 1720, 1320, 1300, 1165, 1065 $cm^{-1}$.

EXAMPLE 6

4β,15-Diacetoxy-3-hydroxyimino-12,13-epoxytrichothec-9-ene and
15-Acetoxy-4β-hydroxy-3-hydroxyimino-12,13-epoxytrichothec-9-ene

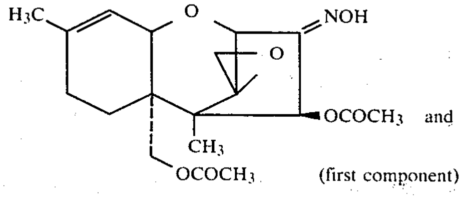
and
(first component)

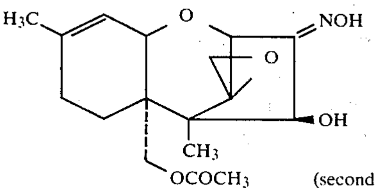
(second component)

To a solution of 4β,15-diacetoxy-12,13-epoxytrichothec-9-en-3-one (364 mg, 1.0 mmol) in 60 ml of methanol was added a solution of hydroxylamine hydrochloride (336 mg, 4.87 mmol) and sodium acetate (336 mg, 2.47 mmol) in 7 ml of water. After 15 hr. of stirring at room temperature the reaction mixture was diluted with $CH_2Cl_2$ (100 ml) and washed with water. The aqueous layer was re-extracted with $CH_2Cl_2$ (2×25 ml). The combined $CH_2Cl_2$ layers were washed with brine and dried over $Na_2SO_4$—$K_2CO_3$. Removal of the solvent gave 333 mg of foam. Chromatography on silica gel (elution with 2% methanol-$CH_2Cl_2$) gave 185 mg (49%) of an amorphous solid after precipitation with diethyl ether and hexane. The NMR and IR spectra indicated that this material was an approximately 2:1 mixture of syn- and anti-oximes of 4β,15-diacetoxy-12,13-epoxytrichothec-9-en-3-one: IR (KBr): 3392, 2986, 2970, 2957, 1741, 1720 (sh), 1673, 1370, 1249, 1032, 918 $cm^{-1}$.

The second component (49 mg, 15%) eluted with 3% methanol-$CH_2Cl_2$ was characterized as an approximately 3:1 mixture of syn- and anti-oximes of 15-acetoxy-4β-hydroxy-12,13-epoxytrichothec-9-en-3-one: IR(KBr): 3410, 2983, 2971, 2955, 1741, 1716 (sh), 1675, 1242, 1047, 963 $cm^{-1}$.

EXAMPLE 7

15-Acetoxy-3α-hydroxy-3β,4β-O,O-ethylidene-12,13-epoxytrichothec-9-ene

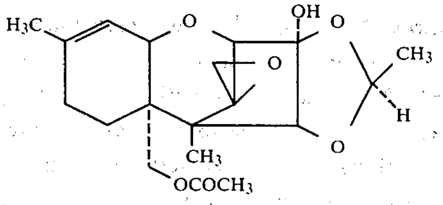

Sodium cyanoborohydride (126 mg, 2 mmol) was added to a solution of 4β,15-diacetoxy-12,13-epoxytrichothec-9-en-3-one (364 mg, 1 mmol) in 6 ml of tetrahydrofuran and 15 ml of isopropyl alcohol containing a small amount of methyl orange. Isopropyl alcohol saturated with HCl was added dropwise until the pH of the reaction media remained approximately 3. After 3 hr. of stirring at room temperature, the resulting mixture was diluted with 30 ml of $CH_2Cl_2$ and washed with water. Drying over $Na_2SO_4$ and removal of the solvent gave 338 mg of oil. This oil was purified by chromatography on silica gel, eluting with pentaneethylacetate (1:1), followed by recrystallization from diethyl ether to give 136 mg (37%) of colorless crystals: mp 172°-173°; IR (KBr): 3410, 2960, 2925, 1745, 1442, 1405, 1306, 1233, 1124, 1067, 1034 $cm^{-1}$.

Anal. Calc'd. for $C_{19}H_{26}O_7$: C, 62.28; H, 7.15. Found: C, 62.05; H, 7.11.

EXAMPLE 8

If the general procedure of Example 1 is repeated with the 4β,15-dichloroacetoxy-3α-hydroxy-12,13-epoxytrichothec-9-ene used therein replaced by an equimolar amount of a 3α-hydroxy ester listed below, there is produced the corresponding 3-keto ester product.

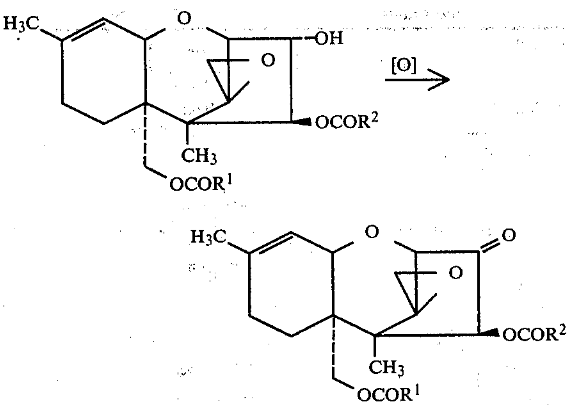

| $R^1$ | $R^2$ |
|---|---|
| $-CH_3$ | $-\underset{\displaystyle CH_3}{\underset{\vert}{C}}=CH_2$ |
| $-CH_2Br$ | $-CH_2Br$ |
| $-CH_2Cl$ | $-\underset{\displaystyle CH_3}{\underset{\vert}{C}}=CH_2$ |
| $-CH_2CH_3$ | $-CH_2CH_3$ |
| $-CH_2CH_2CH_3$ | $-CH_2CH_2CH_3$ |
| $-CH_2CH_2CH_2CH_3$ | $-CH_2CH_2CH_2CH_3$ |
| $-CH_2CH_2CHClCH_3$ | $-CH_2CH_2CHClCH_3$ |
| $-CH_2CHClCH_3$ | $-CH_2CHClCH_3$ |
| $-CH_2\underset{\displaystyle CH_2Cl}{\underset{\vert}{C}H}CH_3$ | $-CH_2\underset{\displaystyle CH_2Cl}{\underset{\vert}{C}H}CH_3$ |
| $-CCl_3$ | $-CCl_3$ |
| $-CF_3$ | $-CF_3$ |
| 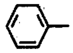 | 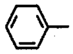 |
| $(CH_3)_2CH-$ | $(CH_3)_2CH-$ |
| 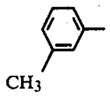 | 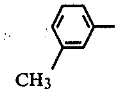 |
| 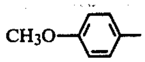 | 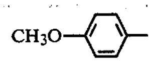 |
| 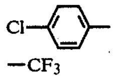 | 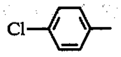 |
| $-CF_3$ | 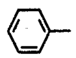 |
| $-CH_3$ | 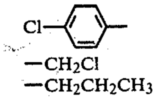 |
| $(CH_3)_2CH-$ | $-CH_2Cl$ |
| 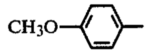 | $-CH_2CH_2CH_3$ |
| 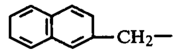 | 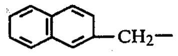 |
| 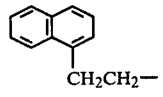 | 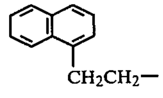 |
| 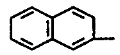 | 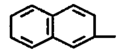 |
| 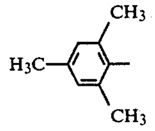 | 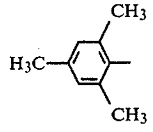 |

-continued

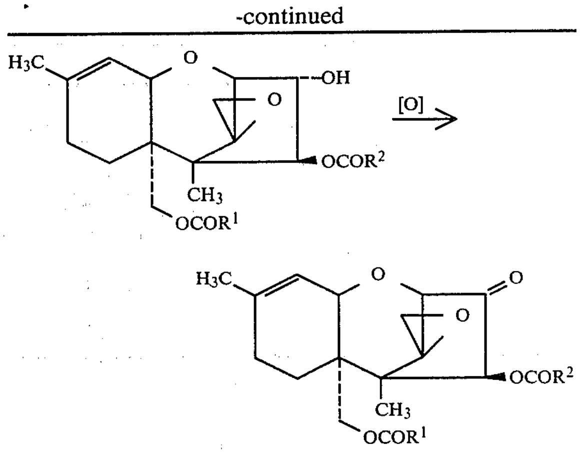

| $R^1$ | $R^2$ |
|---|---|
| 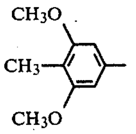 | 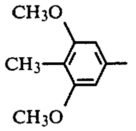 |
| 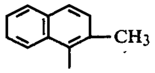 | 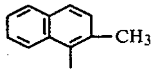 |
| 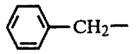 | 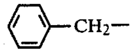 |
| 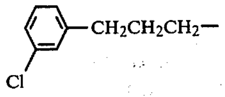 | 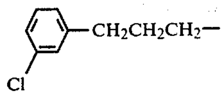 |
| 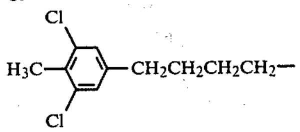 | $-CH_2Cl$ |

EXAMPLE 9

If the general procedure of Example 6 is repeated with the 4β,15-diacetoxy-12,13-epoxytrichothec-9-en-3-one used therein replaced by an equimolar amount of a 3-keto ester listed below, there is produced the corresponding oxime products.

| Starting Material | Products |
|---|---|
| 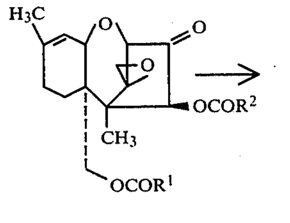 | 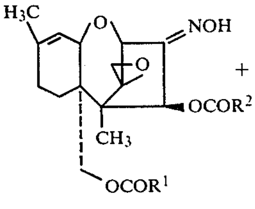 + |

-continued

| Starting Material | Products |
|---|---|
| | 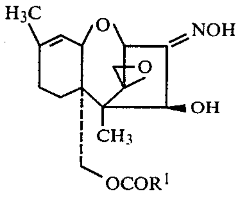 |
| $R^1$ | $R^2$ |
| $-CH_2Cl$ | $-CH_2Cl$ |
| $-CH_3$ | $-CH_2Cl$ |
| $-\underset{CH_3}{C}=CH_2$ | $-\underset{CH_3}{C}=CH_2$ |
| $-\underset{CH_3}{C}=CH_2$ | $-CH_2Cl$ |
| $-CH_3$ | $-\underset{CH_3}{C}=CH_2$ |
| $-CH_2Br$ | $-CH_2Br$ |
| $-CH_2Cl$ | $-\underset{CH_3}{C}=CH_2$ |
| $-CH_2CH_3$ | $-CH_2CH_3$ |
| $-CH_2CH_2CH_3$ | $-CH_2CH_2CH_3$ |
| $-CH_2CH_2CH_2CH_3$ | $-CH_2CH_2CH_2CH_3$ |
| $-CH_2CH_2CHClCH_3$ | $-CH_2CH_2CHClCH_3$ |
| $-CH_2CHClCH_3$ | $-CH_2CHClCH_3$ |
| $-CH_2\underset{CH_2Cl}{CH}CH_3$ | $-CH_2\underset{CH_2Cl}{CH}CH_3$ |
| $-CCl_3$ | $-CCl_3$ |
| $-CF_3$ | $-CF_3$ |
| 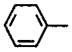 | 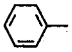 |
| $(CH_3)_2CH-$ | $(CH_3)_2CH-$ |
| 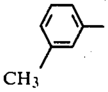 | 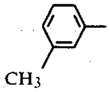 |
| 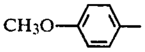 | 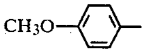 |
| 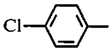 | 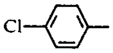 |
| $-CF_3$ | 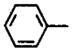 |

-continued

| Starting Material | Products |
|---|---|
| $-CH_3$ | 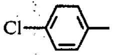 |
| $(CH_3)_2CH-$ | $-CH_2Cl$ |
| 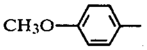 | $-CH_2CH_2CH_3$ |
| 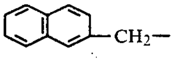 | 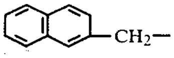 |
| 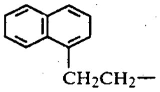 | 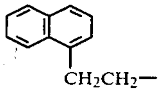 |
| 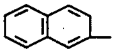 | 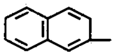 |
| 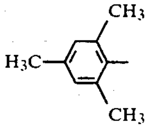 | 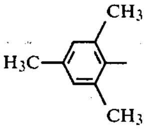 |
| 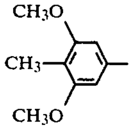 | 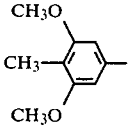 |
| 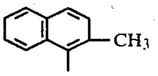 | 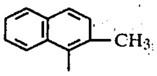 |
| 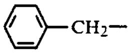 | 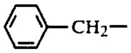 |
| 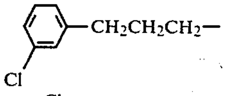 | 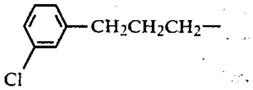 |
| 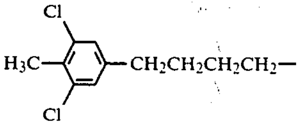 | $-CH_2Cl$ |

We claim:

1. The compound having the formula

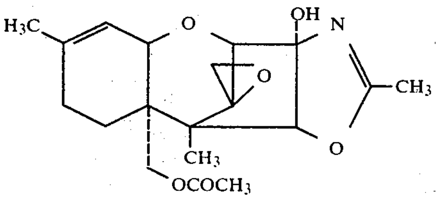

* * * * *